United States Patent [19]

Brooks et al.

[11] Patent Number: 4,772,279
[45] Date of Patent: Sep. 20, 1988

[54] WC-DISPOSABLE BAGS

[75] Inventors: Kenneth J. Brooks; Peter J. Briggs, both of Lancing, England

[73] Assignee: Smiths Industries Public Limited Company, London, England

[21] Appl. No.: 1,733

[22] Filed: Jan. 9, 1987

[30] Foreign Application Priority Data

Jan. 17, 1986 [GB] United Kingdom ............... 8601172
Jan. 25, 1986 [GB] United Kingdom ............... 8601833

[51] Int. Cl.⁴ ............................................ A61F 5/44
[52] U.S. Cl. .................................... 604/339; 604/344
[58] Field of Search ............... 604/332–345; 383/1, 113–116; 128/767

[56] References Cited

U.S. PATENT DOCUMENTS

| | | | |
|---|---|---|---|
| 3,081,771 | 3/1963 | Lee | 604/344 |
| 3,908,658 | 9/1975 | Marson | 604/336 |
| 4,213,458 | 7/1980 | Nolan et al. | 604/344 |
| 4,387,712 | 6/1983 | Briggs et al. | 604/333 |
| 4,620,999 | 11/1986 | Holmes | 604/333 |

FOREIGN PATENT DOCUMENTS

| | | | |
|---|---|---|---|
| 2524306 | 10/1983 | France | 604/317 |
| 2083762 | 3/1982 | United Kingdom | 604/332 |

Primary Examiner—C. Fred Rosenbaum
Assistant Examiner—Mario Costantino
Attorney, Agent, or Firm—Pollock, Vande Sande & Priddy

[57] ABSTRACT

A wc-disposable ostomy bag has an outer water soluble layer of polyvinyl alcohol and an inner relatively insoluble layer of polyvinylidene chloride. A flange of a double-sided pressure-sensitive adhesive ring has one side adhered to the outer layer only, around an opening into the bag so that the edge of the outer layer around the opening is left exposed to material passing through the opening. The other side of the flange in use is secured to the patient's skin around the stoma either directly or via a peristomal wafer.

7 Claims, 3 Drawing Sheets

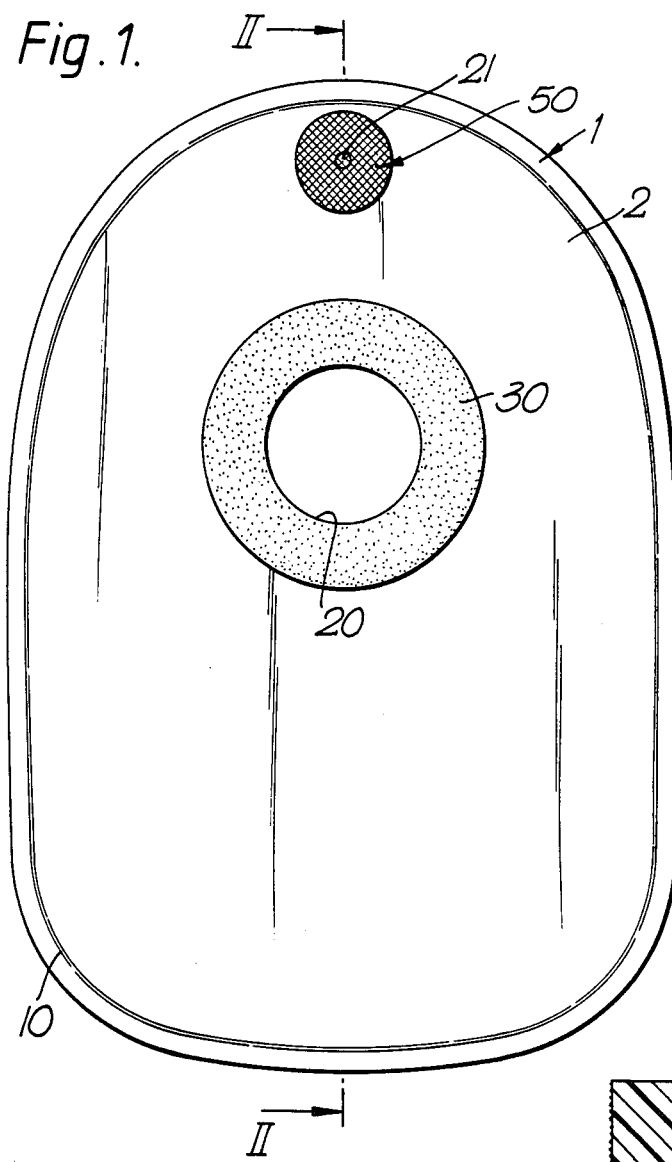
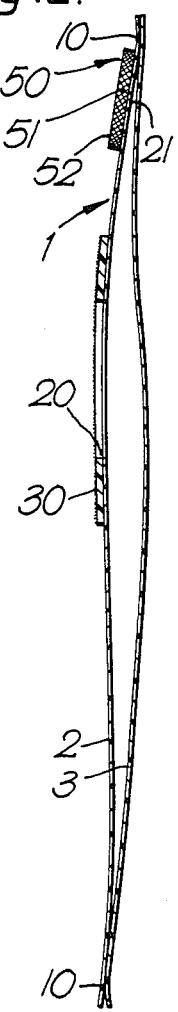
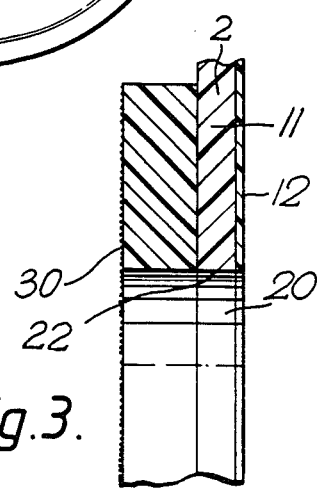
Fig.1.
Fig.2.
Fig.3.

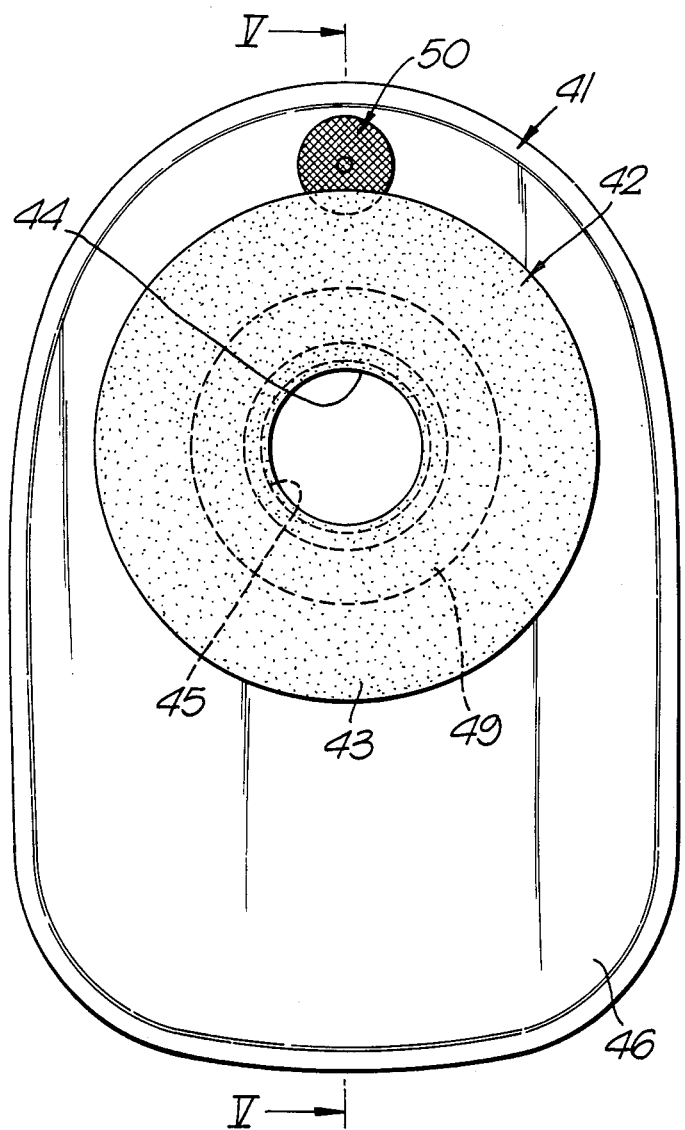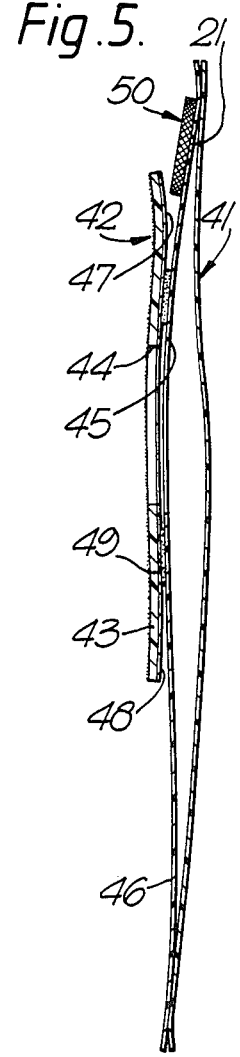
Fig.4.
Fig.5.

WC-DISPOSABLE BAGS

BACKGROUND OF THE INVENTION

This invention relates to wc-disposable bags of the kind having an outer water soluble layer, an inner relatively insoluble layer, an opening into the bag, and a flange around the opening for securing the bag to the patient.

Bodily excretions such as faeces, urine and sputum are now being collected in disposable bags which are more hygenic than reusable containers. Such bags are often used by incontinent patients or by ostomy patients, that is, those who have undergone colostomy, ileostomy or urostomy. After use, disposal of the bag and its contents can cause difficulties. The bags are not usually disposable in a wc because of their size, stiffness and the fact that they tend to float because of entrapped air. More recently, bags have been developed which can be flushed away in a wc. These generally comprise an outer film of water soluble material, which gives mechanical strength to the bag, and an inner film of an insoluble material which protects the outer film from any moisture in the contents of the bag, but which itself is very thin and flexible or has little mechanical strength. Once the outer film has been dissolved, the inner film is either broken up and dispersed by the turbulence in the wc pan or collapses limply about the bag contents, allowing the remnants of the bag and its contents to be flushed away without causing an obstruction.

These bags are secured to the patient by means of a flange around the opening to the bag that is secured to the patient directly or indirectly such as by means of an adhesive or by a mechanical coupling. In previous wc disposable bags, such as described in GB 2083762A, the flange has been arranged to be secured in contact with both the inner and outer surfaces of the bag so that it extends across the exposed edge of the soluble film and thereby protects it from attack by moisture in any matter passing though the opening. The construction and assembly of these flanges is relatively time-consuming and adds significantly to the cost of the completed bags.

It is possible to secure a flange only to the inner film if the outer film is removed from the region around the bag opening. This however, is an additional manufacturing step leading to extra costs. It also weakens the bag if there is a region around the outside of the flange that is not supported by the mechanically stronger outer layer. Furthermore, the thickness and material of the inner film may not be such as to prevent the escape of odour from some bags where the material of the thicker outer film acts as an odour barrier layer. Thus, this construction in some bags can lead to the escape of unpleasant odour from the bag.

SUMMARY OF THE INVENTION

It is the object of the present invention to provide a wc-disposable bag that avoids these disadvantages.

According to one aspect of the present invention there is provided a wc disposable bag having an outer water soluble layer, an inner relatively water insoluble layer, an opening into the bag, and a flange around the opening for securing the bag to the patient, the flange being secured to contact the outer water soluble layer only, leaving the edge of the water soluble layer exposed around the opening to material passing through the opening.

In this way, assembly of the flange on the bag is simplified and costs can be reduced. Although the water soluble film is exposed to material passing through the opening, the rate at which the film is dissolved has been found to be relatively slow by comparison with the time the bag is in use because only the edge is exposed. The problem of odour is also obviated.

The flange is preferably secured to the outer water soluble layer by an adhesive. The flange may have an adhesive surface which in use is secured to the patient. The flange may include a double-sided ring of adhesive material one side of which is adhered to the outer water soluble layer. The flange may include a disc having a central aperture therethrough, the ring being adhered to only a central portion of one side of the disc around the aperture such that an outer portion of the disc is unattached to the bag, the other side of the disc being of a pressure-sensitive adhesive material.

The outer water soluble layer is preferably of polyvinyl alcohol. The inner relatively water insoluble layer may be of polyvinylidene chloride.

A wc-disposable ostomy bag in accordance with the present invention, will now be described, by way of example, with reference to the accompanying drawings.

DETAILED DESCRIPTION OF THE DRAWINGS

FIG. 1 is an elevation view showing the front of the the bag;

FIG. 2 is a sectional side elevation of the bag of FIG. 1 along the line II—II;

FIG. 3 is a sectional side elevation to a larger scale showing a part of the bag in greater detail;

FIG. 4 is a front elevation of an alternative bag;

FIG. 5 is a side elevation of the bag of FIG. 4, along the line V—V; and

DETAILED DESCRIPTION

Figure 6:
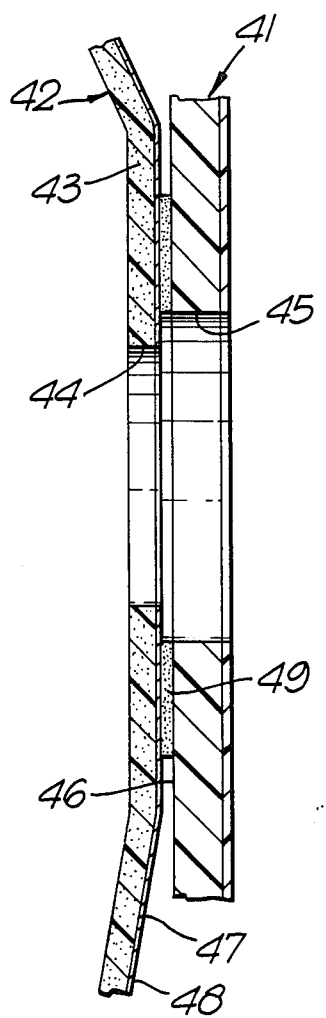
FIG. 6 is a sectional side elevation to a larger scale showing a part of FIG. 5 in greater detail.

With reference first to FIGS. 1 and 2, there is shown a wc-disposable ostomy bag 1 of generally oblong shape formed by sealing two flexible sheets 2 and 3 together around their edge 10. A circular aperture 20 of between about 19 mm to 64 mm in diameter is formed in the front sheet 2, to provide an opening for the bag. A smaller vent 21, about 2 mm in diameter, is formed close to the top of the bag to allow for the escape of gas. The bag also has a filter 50 over the vent 21 to reduce odour from escaping flatus. The filter may comprise a disc 51 of activated carbon fabric, larger than the vent 21, and an impervious disc of plastic 52 covering the flat surface of the disc and leaving its edge exposed. In this way, gas emerging through the vent 21 passes radially through the disc 51 and out of its exposed edge. As so far described, the bag is entirely conventional.

With reference now also to FIG. 3, the sheets 2 and 3 are both of the same material, each being made of two layers or films 11 and 12. One film 11 is of a cold-water soluble polyvinyl alcohol containing about 12% by weight glycerol, the other film 12 is thinner being impermeable to water and may be of, for example, polyvinylidene chloride. The two sheets 2 and 3 are secured together in such a way that the impermeable film 12 provides the inner surface of the bag, whilst the polyvinyl alcohol film 11 is exposed on the outer surface of the bag. The inner film 12 is relatively impermeable to gases and provides an effective odour barrier.

The bag 1 includes a flange 30 around the opening 20 which is used to secure the bag to the patient's skin around the ostomy. In the arrangement shown in FIGS. 1 to 3 the flange 30 is simply a flat, double-sided ring of pressure-sensitive adhesive material, one side of which is secured in contact with only the outer film 11 of the bag, and the other side of which, in use, is secured to the patient's skin either directly or via a peristomal wafer. The internal diameter of the ring is approximately the same as that of the opening 20, the external diameter being about 26 mm larger.

In use, the inner film 12 protects the outer film 11 from being dissolved by the contents of the bag. It will, however, be seen that an edge 22 of the outer film is exposed at the opening 20 between the flange 30 and the inner film 12. The exposed edge 22 will be subject to the dissolving action of moisture in matter entering the bag through the opening 20. Because, however, the edge area is small, the rate at which the outer film 11 is dissolved at this point will be very low by appropriately selecting the appropriate grade of polyvinyl alcohol. Although this would eventually lead to detachment of the flange 30, it has been found in practice that this take several days or weeks to occur. Ostomy bags are replaced at least once a day so this does not cause any problems to the user.

Because the flange 30 is secured only to the outer water-soluble film 11, this makes assembly considerably simpler than that of previous bags with a water-soluble outer film, where the flange is arranged to extend over and protect the exposed edge of the outer film at the opening. The arrangement of the present invention, also avoids the disadvantages mentioned above, of a bag in which the flange is secured only to the inner film by removal of an annular region of the outer film around the opening of the bag.

After use, when the bag has been filled, and removed, it is folded in half along its length, that is along the line II—II, with the front sheet 2 innermost. In this way, the two halves of the adhesive flange 30 overlie and adhere to one another, thereby sealing the opening 20. The user then squeezes the bag to expel trapped gas through the filter 50, drops it into the pan of a water closet and flushes it away. The water and the turbuluence produced by flushing rapidly cause the outer film 11 to dissolve leaving the inner film 12 surrounding the contents of the bag. Because the inner film 12 is mechanically weak, once it loses the structural support provided by the outer film 11, it breaks up under the action of the turbulent water in the wc pan thereby allowing the bag to be freely flushed down the waste outlet of the wc without floating or causing obstruction. The flange 30 is also wc-disposable either by being made of a material that is broken up in the wc pan or because it is small enough and flexible enough to slip along the waste outlet without causing obstructions.

An alternative bag 41 is shown in FIGS. 4 to 6. This bag 41 is of the same shape and material as the bag shown in FIGS. 1 to 3 but differs in the construction of the flange 42 by which the bag is secured to the patient. The flange 42 comprises an annular adhesive disc 43 with an external diameter of about 110 mm and a central aperture 44 slightly smaller than the opening 45 in the front wall 46 of the bag 41. The rear side 47 of the disc 43 is covered by a non-adhesive backing sheet 48, the disc 43 being secured to the wall 46 by means of a smaller ring 49 of double-sided adhesive material forming a part of the flange 42 and interposed between the backing sheet 48 and the front wall of the bag 41. This ring 49 has a smaller outer diameter than the disc 43 so that the flange 42 remains unattached to the bag 41 at its outer edge. A flange of this kind provides a larger surface area of adhesive and obviates the need for any mechanical coupling to support the bag, of the kind sometimes required with bags of the kind shown in FIGS. 1 to 3.

Various other bags may be provided in accordance with the present invention. A flange may be secured to the outer water-soluble surface of the bag by welding, instead of by adhesive. The flange need not necessarily be provided with an adhesive layer since a mechanical coupling could be used to secure the bag to the user.

Alternative materials could be used to provide the water soluble and impermeable films on the outside and inside of the bag.

What we claim is:

1. A wc-disposable bag comprising: an outer water soluble layer; an inner relatively water insoluble layer; an opeining into the bag by which material from a patient can enter the bag; a flange having means for securing the bag to the patient; and means for securing said flange around the opening to contact the water soluble layer only, leaving an edge of the water soluble layer exposed around the opening to material passing through the opening.

2. A wc-disposable bag according to claim 1, wherein said means for securing the bag to the patient includes an adhesive surface on the flange.

3. A wc-disposable bag according to claim 1, wherein said outer water soluble layer is of polyvinyl alcohol.

4. A wc-disposable bag according to claim 1, wherein the inner relatively water insoluble layer is of polyvinylidene chloride.

5. A wc-disposable bag according to claim 1, wherein said means for securing the flange to the water soluble layer includes an adhesive.

6. A wc-disposable bag according to claim 5, wherein said flange includes a double-sided ring of adhesive material one side of which is adhered to the outer water soluble layer.

7. A wc-disposable bag according to claim 6, wherein the flange includes a disc, said disc having a central aperture therethrough, wherein said ring is adhered to only a central portion of one side of said disc around said aperture such that an outer portion of said disc is unattached to the bag, and wherein the other side of the disc is of a pressure-sensitive adhesive material.

* * * * *